United States Patent [19]
Ashraf

[11] Patent Number: 5,858,019
[45] Date of Patent: Jan. 12, 1999

[54] GRAFT SITE CUTTER

[76] Inventor: Bahman Ashraf, 120 Wood Ave. S., Suite 305, Iselin, N.J. 08830

[21] Appl. No.: 951,131

[22] Filed: Oct. 15, 1997

[51] Int. Cl.⁶ .................................................. A61B 17/32
[52] U.S. Cl. .............................. 606/167; 606/1; 606/186; 606/187; 604/173; 623/15
[58] Field of Search ................................. 606/167, 186, 606/187, 1; 604/173; 623/15

[56] References Cited

U.S. PATENT DOCUMENTS

| | | | |
|---|---|---|---|
| 5,439,475 | 8/1995 | Bennet | 606/187 |
| 5,643,308 | 7/1997 | Markman | 606/187 |
| 5,662,661 | 9/1997 | Boudjema | 606/167 |

Primary Examiner—Michael Powell Buiz
Assistant Examiner—Vy Quang Bui

[57] ABSTRACT

A surgical device comprises a first horizontal flat spongy flexible layer having upper and lower surfaces. A second horizontal flat plastic layer also has upper and lower surfaces, the upper surface of the second layer being secured to the lower surface of the first layer. A third horizontal flat spongy flexible layer also has upper and lower surfaces, the upper surface of the third layer being secured to the lower surface of the second layer. A plurality of surgical cutting units are imbedded in the layers in spaced apart positions, each unit having a plurality of knife elements having downwardly extending cutting points disposed within the third layer adjacent the lower surface.

6 Claims, 2 Drawing Sheets

GRAFT SITE CUTTER

BACKGROUND OF THE INVENTION

In order to implant hair elements into bald regions of the scalp of a patient, the hair elements are removed from other portions of the body of the patent and are surgically implanted into extremely small openings previously cut into the bald regions. Presently, such openings are surgically cut individually and sequentially.

The present invention is directed toward a surgical device which can be used by a surgeon to cut a plurality of such openings simultaneously in said bald regions, thereby enabling faster hair implanting operations.

SUMMARY OF THE INVENTION

In accordance with the principles of this invention, the surgical device comprises a first horizontal flat spongy flexible layer having upper and lower surfaces. A second horizontal flat plastic layer also has upper and lower surfaces, the upper surface of the second layer being secured to the lower surface of the first layer. A third horizontal flat spongy flexible layer also has upper and lower surfaces, the upper surface of the third layer being secured to the lower surface of the second layer. A plurality of surgical cutting units are imbedded in the layers in spaced apart positions, each unit having a plurality of knife elements having downwardly extending cutting points disposed within the third layer adjacent the lower surface.

When the device is disposed for use in engagement with a selected portion of the scalp of a patient, a surgeon presses down upon the first layer and causes the points of the knife elements to be moved out of the third layer to engage said selected portion of the scalp.

In this manner, the present procedure for individually and sequentially cutting openings for hair transplants can be replaced through use of the present invention which enables a surgeon to cut a plurality of such openings simultaneously in said bald regions, thereby enabling faster hair implanting operations.

The selected portion of the scalp may be curved and the device is sufficently flexible to be curved to conform to the scalp curvature. A manually adjustable frame can be used to engage and surround the device to hold it in such curved position during use.

Other objects and advantages of this invention will either be explained or will become apparent hereinafter.

DETAILED DESCRIPTION OF PREFERRED EMBODIMENTS

Figure 1:
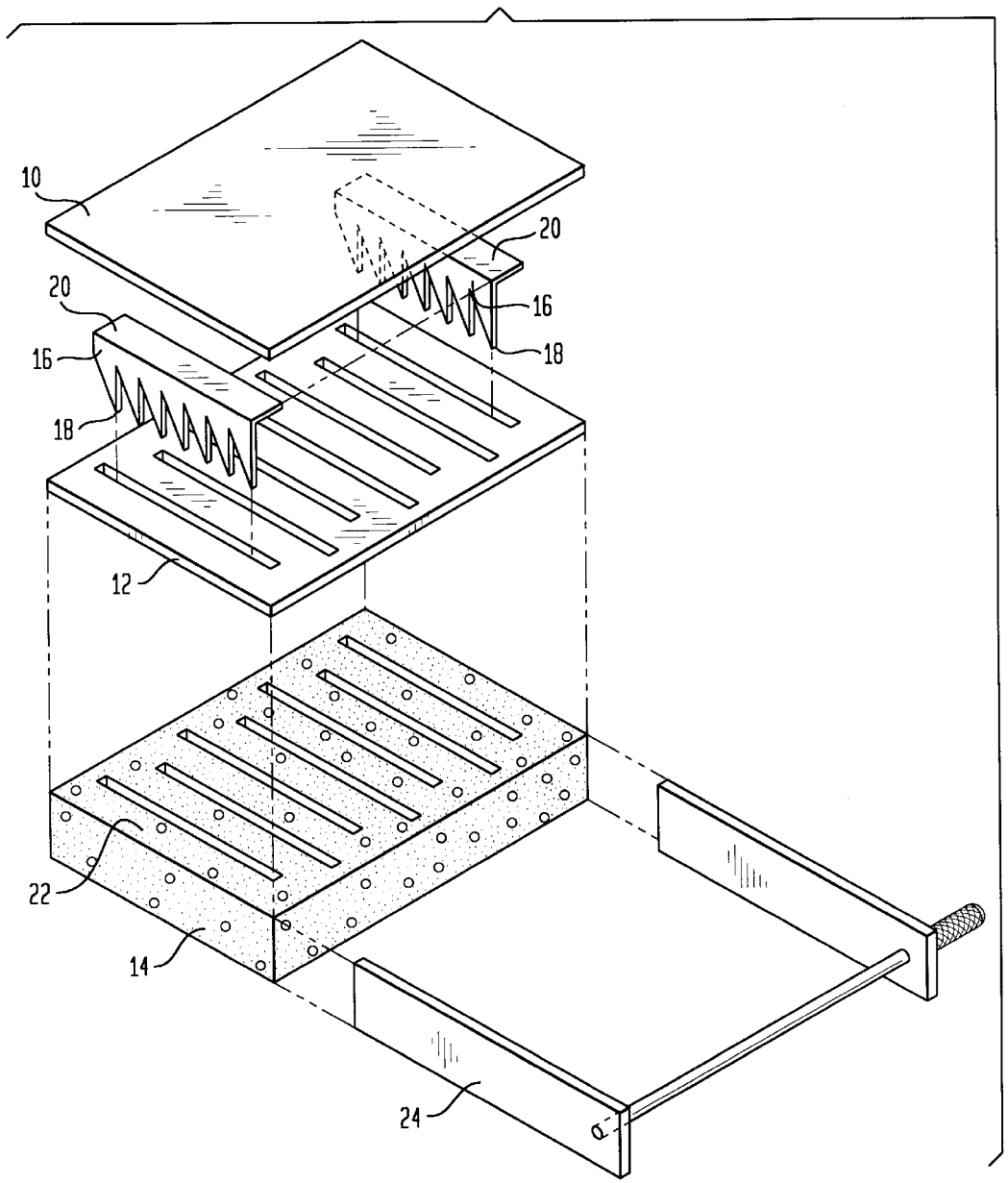
FIG. 1 is an exploded view of a preferred embodiment of the invention.
Figure 2:
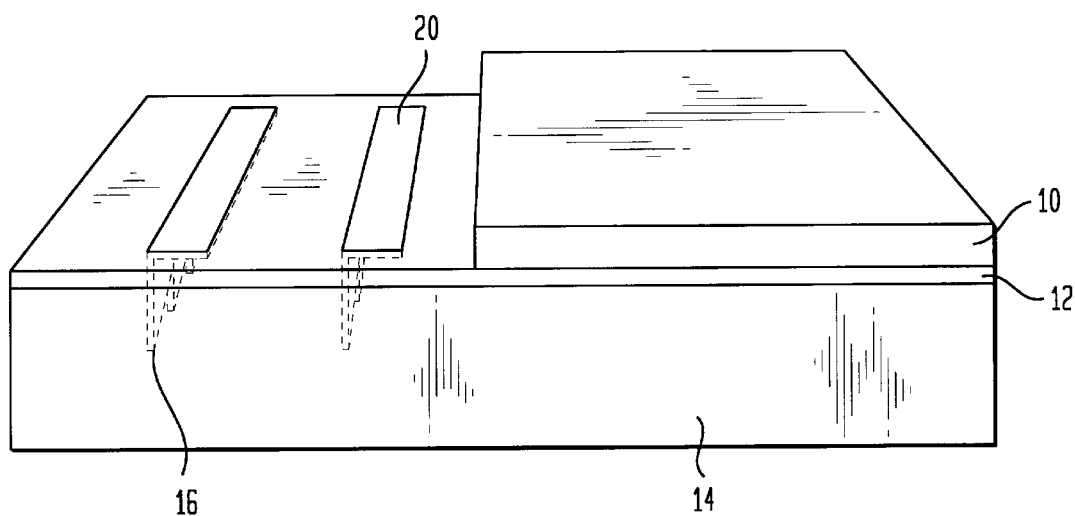
FIG. 2 is a partially cut away assembled view of the invention shown in FIG. 1 with the knife elements concealed.
Figure 3:
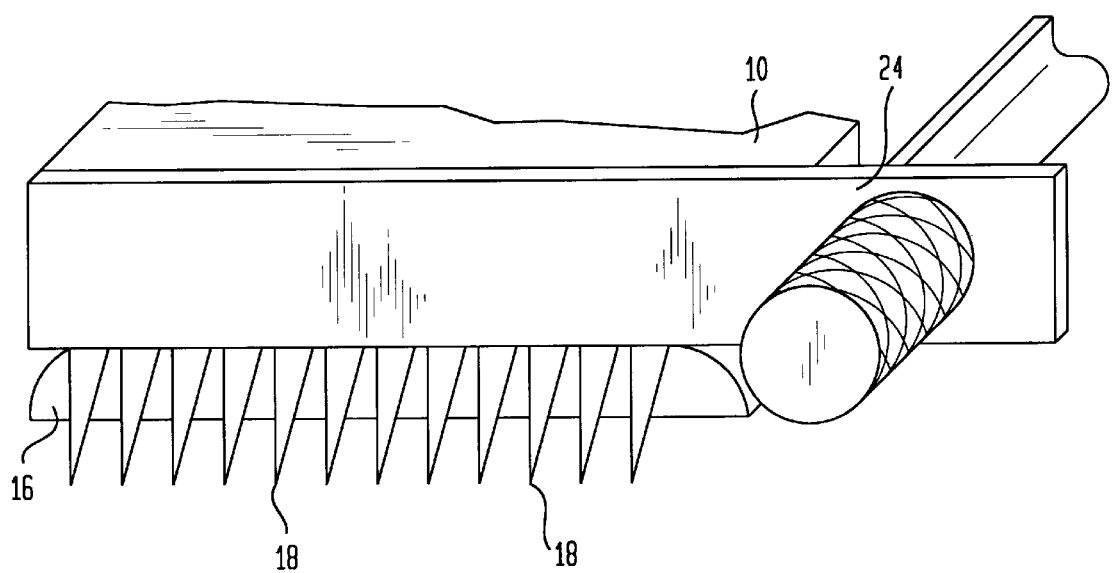
FIG. 3 is a side view of the invention partially in cross section with the knife elements extended.

Referring now to FIGS. 1–3, the surgical device utilizes a first horizontal flat spongy flexible layer 10 having upper and lower surfaces. A second horizontal flat plastic layer 12 also has upper and lower surfaces. The upper surface of the second layer is secured to the lower surface of the first layer. A third horizontal flat spongy flexible layer 14 also has upper and lower surfaces. The upper surface of the third layer is secured to the lower surface of the second layer.

A plurality of surgical cutting units are imbedded in the layers in spaced apart positions, each unit having a plurality of knife elements 16 which have downwardly extending cutting points 18 disposed within the third layer adjacent the lower surface.

Each cutting unit has a flat horizontal member 20 to which the knife elements are secured and extend downwardly therefrom, these members being disposed in spaced apart position between the first and second layers. The knife elements in each unit are secured to each other and define a common vertical plane, the vertical planes for each unit being parallel.

The third layer has a plurality of horizontally elongated slots 22 equal in number to the plurality of units, the knife elements in each unit engaging a corresponding slot.

When the device is disposed for use in engagement with a selected portion of the scalp of a patient, a surgeon presses down upon the first layer and causes the points of the knife elements to be moved out of the third layer to engage said selected portion of the scalp.

The device is further provided with a manually adjustable frame or clamp 24 which engages and surrounds the device to hold it in engagement with a selected portion of the scalp of a patient when the device is to be used.

While the invention has been described with particular reference to the drawings and preferred embodiment, the protection solicited is to be limited only by the terms of the claims which follow.

What is claimed is:

1. A surgical device comprising:

a first horizontal flat spongy flexible layer having upper and lower surfaces;

a second horizontal flat plastic layer having upper and lower surfaces, the upper surface of the second layer being secured to the lower surface of the first layer;

a third horizontal flat spongy flexible layer having upper and lower surfaces, the upper surface of the third layer being secured to the lower surface of the second layer; and a plurality of surgical cutting units imbedded in the layers in spaced apart positions, each unit having a plurality of knife elements having downwardly extending cutting points disposed within the third layer adjacent the lower surface.

2. The device of claim 1 wherein each cutting unit has a flat horizontal member to which the knife elements are secured and extend downwardly therefrom, these members being disposed in spaced apart position between the first and second layers.

3. The device of claim 2 wherein the knife elements in each unit are secured to each other and define a common vertical plane, the vertical planes for each unit being parallel.

4. The device of claim 3 wherein the third layer has a plurality of horizontally elongated slots equal in number to the plurality of units, the knife elements in each unit engaging a corresponding slot.

5. The device of claim 4 wherein when disposed for use in engagement with a selected portion of the scalp of a patient, a surgeon presses down upon the first layer and causes the points of the knife elements to be moved out of the third layer to engage said selected portion of the scalp.

6. The device of claim 4 which is further provided with a manually adjustable frame engaging and surrounding the device to hold it in engagement with a selected portion of the scalp of a patient when the device is to be used.

* * * * *